US006127124A

United States Patent [19]
Leeds et al.

[11] Patent Number: 6,127,124
[45] Date of Patent: Oct. 3, 2000

[54] FLUORESCENCE BASED NUCLEASE ASSAY

[75] Inventors: Janet M. Leeds, Encinitas; Lendell L. Cummins, San Deigo, both of Calif.

[73] Assignee: Isis Pharmaceuticals, Inc., Carlsbad, Calif.

[21] Appl. No.: 09/234,237

[22] Filed: Jan. 20, 1999

[51] Int. Cl.[7] .............................. G01N 33/00; C12Q 1/68; C12P 19/34; C07H 21/04
[52] U.S. Cl. ............................ 435/6; 536/23.1; 536/23.2; 435/91.1; 436/94
[58] Field of Search ......................... 435/6, 91.1; 436/94; 536/23.2, 23.1

[56] References Cited

U.S. PATENT DOCUMENTS

| | | | |
|---|---|---|---|
| 3,687,808 | 8/1972 | Merigan et al. | 435/91.3 |
| 4,469,863 | 9/1984 | Ts'o et al. | 536/24.5 |
| 4,476,301 | 10/1984 | Imbach et al. | 536/25.2 |
| 4,587,044 | 5/1986 | Miller et al. | 530/322 |
| 4,605,735 | 8/1986 | Miyoshi et al. | 536/26.3 |
| 4,667,025 | 5/1987 | Miyoshi et al. | 536/26.3 |
| 4,762,779 | 8/1988 | Snitman | 435/6 |
| 4,789,737 | 12/1988 | Miyoshi et al. | 536/23.1 |
| 4,824,941 | 4/1989 | Gordon et al. | 530/403 |
| 4,828,979 | 5/1989 | Klevan et al. | 435/6 |
| 4,835,263 | 5/1989 | Nguyen et al. | 536/24.3 |
| 4,845,205 | 7/1989 | Huynh Dinh et al. | 536/25.34 |
| 4,876,335 | 10/1989 | Yamane et al. | 536/24.3 |
| 4,904,582 | 2/1990 | Tullis | 435/6 |
| 4,948,882 | 8/1990 | Ruth | 536/25.2 |
| 4,958,013 | 9/1990 | Letsinger | 536/24.5 |
| 5,013,830 | 5/1991 | Ohtsuka et al. | 536/25.1 |
| 5,023,243 | 6/1991 | Tullis | 514/44 |
| 5,034,506 | 7/1991 | Summerton et al. | 528/391 |
| 5,082,830 | 1/1992 | Brakel et al. | 435/6 |
| 5,109,124 | 4/1992 | Ramachandran et al. | 536/24.3 |
| 5,112,963 | 5/1992 | Pieles et al. | 536/25.32 |
| 5,118,802 | 6/1992 | Smith et al. | 536/24.3 |
| 5,130,302 | 7/1992 | Spielvogel et al. | 514/45 |
| 5,134,066 | 7/1992 | Rogers et al. | 435/91.3 |
| 5,138,045 | 8/1992 | Cook et al. | 536/24.5 |
| 5,149,797 | 9/1992 | Pederson et al. | 536/23.1 |
| 5,166,315 | 11/1992 | Summerton et al. | 528/406 |
| 5,175,273 | 12/1992 | Bischofberger et al. | 536/26.13 |
| 5,185,444 | 2/1993 | Summerton et al. | 544/81 |
| 5,188,897 | 2/1993 | Suhadolnik et al. | 428/402.2 |
| 5,214,134 | 5/1993 | Weis et al. | 536/25.3 |
| 5,214,136 | 5/1993 | Lin et al. | 514/44 |
| 5,216,141 | 6/1993 | Benner | 536/27.13 |
| 5,218,105 | 6/1993 | Cook et al. | 536/25.31 |
| 5,220,007 | 6/1993 | Pederson et al. | 536/23.1 |
| 5,235,033 | 8/1993 | Summerton et al. | 528/391 |
| 5,245,022 | 9/1993 | Weis et al. | 536/24.5 |
| 5,254,469 | 10/1993 | Warren, III et al. | 435/188 |
| 5,256,775 | 10/1993 | Froehler | 536/25.6 |
| 5,258,506 | 11/1993 | Urdea | 536/23.1 |
| 5,262,536 | 11/1993 | Hobbs, Jr. | 546/25 |
| 5,264,423 | 11/1993 | Cohen et al. | 514/44 |
| 5,264,562 | 11/1993 | Matteucci | 536/23.1 |
| 5,264,564 | 11/1993 | Matteucci | 536/23.1 |
| 5,272,250 | 12/1993 | Spielvogel et al. | 530/300 |
| 5,276,019 | 1/1994 | Cohen et al. | 514/44 |
| 5,278,302 | 1/1994 | Caruthers et al. | 536/24.5 |
| 5,286,717 | 2/1994 | Cohen et al. | 514/44 |
| 5,292,873 | 3/1994 | Rokita et al. | 536/24.3 |
| 5,317,098 | 5/1994 | Shizuya et al. | 536/23.1 |
| 5,321,131 | 6/1994 | Agrawal et al. | 536/25.34 |
| 5,366,878 | 11/1994 | Pederson et al. | 435/91.3 |
| 5,367,066 | 11/1994 | Urdea et al. | 536/24.3 |
| 5,371,241 | 12/1994 | Brush et al. | 549/220 |
| 5,391,723 | 2/1995 | Priest | 536/23.1 |
| 5,399,676 | 3/1995 | Froehler | 536/23.1 |
| 5,403,711 | 4/1995 | Walder et al. | 435/6 |
| 5,405,938 | 4/1995 | Summerton et al. | 528/406 |
| 5,405,939 | 4/1995 | Suhadolnik et al. | 530/322 |
| 5,414,077 | 5/1995 | Lin et al. | 536/24.3 |
| 5,416,203 | 5/1995 | Letsinger | 536/25.34 |
| 5,432,272 | 7/1995 | Benner | 536/25.3 |

(List continued on next page.)

FOREIGN PATENT DOCUMENTS

WO 92/03464 3/1992 WIPO.

OTHER PUBLICATIONS

Stebbins et al., Temporal analysis of DNA restriction digests by capillary electrophoresis, Journal of Chromatography B, vol. 697, pp. 181–188, 1997.

Saevels et al., Capillary Electrophoresis of RNA oligonucleotides . . . , Analytical Biochemistry vol. 266, pp. 93–101, Jan. 1999.

Saevels et al., In–line couplin of the enzymatic degradation of oligonucleotides with capillary polymer sieving electrophoresis, vol. 69, No. 16, pp. 3299–3303, Aug. 1997.

Amann et al., "Modern methods in subsurface microbiology: in situ identification of microorganisms with nucleic acid probes", *Microbiol. Rev.*, 1997, 20, 191–200.

Bruin et al., "Stability measurements of antisense oligonucleotides by capillary gel electrophoresis", *J. Chromatogr.*, 1995, 709, 181–195.

Chen et al., "Identification of DNA molecules by pre–column hybridization using capillary electrophoresis", *J. Chromatogr.*, 1991, 559, 295–305.

(List continued on next page.)

*Primary Examiner*—George C. Elliott
*Assistant Examiner*—Janet L. Epps
*Attorney, Agent, or Firm*—Woodcock Washburn Kurtz Mackiewicz & Norris LLP

[57] ABSTRACT

Methods for the determination of nuclease stability of an oligomeric compound and its deletion sequences by capillary gel electrophoresis using laser-induced fluorescence detection (LIF CGE) are provided. Fluorescently labeled oligomeric compounds are treated with one or more agents having nuclease activity resulting in an assay mixture of the original oligomeric compound and its deletion sequences. A diluted aliquot taken directly from the assay mixture is analyzed using LIF CGE. Results of the assay yield quantitative concentrations of the oligomeric compound and each of the deletion sequences. In further embodiments, the invention provides methods for determining the relative binding affinity of one or more oligomeric compounds for a substrate having nuclease activity, and methods for determining the nuclease activity of an enzyme.

46 Claims, No Drawings

U.S. PATENT DOCUMENTS

| | | | |
|---|---|---|---|
| 5,434,257 | 7/1995 | Matteucci et al. | 536/24.3 |
| 5,451,463 | 9/1995 | Nelson et al. | 428/402 |
| 5,453,496 | 9/1995 | Caruthers et al. | 536/24.5 |
| 5,455,233 | 10/1995 | Spielvogel et al. | 514/44 |
| 5,457,187 | 10/1995 | Gmeiner et al. | 536/25.5 |
| 5,459,255 | 10/1995 | Cook et al. | 536/27.13 |
| 5,466,677 | 11/1995 | Baxter et al. | 514/44 |
| 5,470,967 | 11/1995 | Huie et al. | 536/24.3 |
| 5,476,925 | 12/1995 | Letsinger et al. | 536/23.1 |
| 5,484,908 | 1/1996 | Froehler et al. | 536/24.31 |
| 5,486,603 | 1/1996 | Buhr | 536/24.3 |
| 5,489,677 | 2/1996 | Sanghvi et al. | 536/24.1 |
| 5,491,133 | 2/1996 | Walder et al. | 514/44 |
| 5,502,177 | 3/1996 | Matteucci et al. | 536/26.6 |
| 5,510,475 | 4/1996 | Agrawal et al. | 536/24.3 |
| 5,512,439 | 4/1996 | Hornes et al. | 435/6 |
| 5,512,667 | 4/1996 | Reed et al. | 536/24.31 |
| 5,514,785 | 5/1996 | Van Ness et al. | 536/22.1 |
| 5,519,126 | 5/1996 | Hecht | 536/24.5 |
| 5,525,465 | 6/1996 | Haralambidis et al. | 435/6 |
| 5,525,711 | 6/1996 | Hawkins et al. | 536/22.1 |
| 5,536,821 | 7/1996 | Agrawal et al. | 536/22.1 |
| 5,541,306 | 7/1996 | Agrawal et al. | 536/22.1 |
| 5,541,307 | 7/1996 | Cook et al. | 536/23.1 |
| 5,541,313 | 7/1996 | Ruth | 536/24.3 |
| 5,545,730 | 8/1996 | Ureda et al. | 536/28.51 |
| 5,550,111 | 8/1996 | Suhadolnik et al. | 514/44 |
| 5,552,538 | 9/1996 | Urdea et al. | 536/24.3 |
| 5,552,540 | 9/1996 | Haralambidis | 536/25.34 |
| 5,561,225 | 10/1996 | Maddry et al. | 536/23.1 |
| 5,563,253 | 10/1996 | Agrawal et al. | 536/22.1 |
| 5,565,350 | 10/1996 | Kmiec | 435/463 |
| 5,565,552 | 10/1996 | Magda et al. | 534/11 |
| 5,567,810 | 10/1996 | Weis et al. | 536/25.3 |
| 5,571,799 | 11/1996 | Tkachuk et al. | 514/47 |
| 5,574,142 | 11/1996 | Meyer, Jr. et al. | 536/23.1 |
| 5,578,717 | 11/1996 | Ureda et al. | 536/26.1 |
| 5,578,718 | 11/1996 | Cook et al. | 536/27.21 |
| 5,580,731 | 12/1996 | Chang et al. | 435/6 |
| 5,585,481 | 12/1996 | Arnold, Jr. et al. | 536/25.34 |
| 5,587,361 | 12/1996 | Cook et al. | 514/44 |
| 5,587,371 | 12/1996 | Sessler et al. | 514/185 |
| 5,587,469 | 12/1996 | Cook et al. | 536/23.1 |
| 5,591,584 | 1/1997 | Chang et al. | 435/6 |
| 5,594,121 | 1/1997 | Froehler et al. | 536/23.5 |
| 5,595,726 | 1/1997 | Magda et al. | 424/9.61 |
| 5,596,086 | 1/1997 | Matteucci et al. | 536/22.1 |
| 5,596,091 | 1/1997 | Switzer | 536/24.5 |
| 5,597,696 | 1/1997 | Linn et al. | 435/6 |
| 5,599,923 | 2/1997 | Sessler et al. | 540/145 |
| 5,599,928 | 2/1997 | Hemmi et al. | 540/474 |
| 5,602,240 | 2/1997 | De Mesmaeker et al. | 536/23.1 |
| 5,608,046 | 3/1997 | Cook et al. | 536/23.1 |
| 5,610,289 | 3/1997 | Cook et al. | 536/25.34 |
| 5,614,617 | 3/1997 | Cook et al. | 536/23.1 |
| 5,618,704 | 4/1997 | Sanghvi et al. | 435/91.5 |
| 5,623,065 | 4/1997 | Cook et al. | 536/23.1 |
| 5,623,070 | 4/1997 | Cook et al. | 536/27.6 |
| 5,625,050 | 4/1997 | Beaton et al. | 536/24.1 |
| 5,633,360 | 5/1997 | Bischofberger et al. | 536/22.1 |
| 5,652,355 | 7/1997 | Metelev et al. | 536/24.5 |
| 5,652,356 | 7/1997 | Agrawal | 536/24.5 |
| 5,663,312 | 9/1997 | Chaturvedula | 536/22.1 |
| 5,677,437 | 10/1997 | Teng et al. | 536/23.1 |
| 5,677,439 | 10/1997 | Weis et al. | 536/23.1 |
| 5,681,941 | 10/1997 | Cook et al. | 536/23.1 |
| 5,688,941 | 11/1997 | Cook et al. | 536/25.3 |
| 5,697,248 | 12/1997 | Brown et al. | 73/290 |
| 5,700,922 | 12/1997 | Cook | 536/23.1 |
| 5,750,692 | 5/1998 | Cook et al. | 544/253 |
| 5,955,589 | 9/1999 | Cook et al. | 536/23.1 |
| 6,043,352 | 3/2000 | Manoharan et al. | 536/24.2 |

OTHER PUBLICATIONS

Chmelik et al., "Characterization of dextrans by size–exclusion chromatography on unmodified silica gel columns, with light–scattering detection, and capillary electrophoresis with laser–induced fluorescence detection", *J. Chromatogr.*, 1997, 790, 93–100.

Crooke, S.T. et al., "Pharmacokinetic Properties of Several Novel Oligonucleotide Analogs in mice", *J. Pharmacol. Exp. Therapeutics*, 1996, 277, 923–937.

De Mesmaeker, A. et al., "Antisense Oligonucleotides", *Acc. Chem. Res.*, 1995, 28, 366–374.

Englisch, U. et al., "Chemically Modified Oligonucleotides as Probes and Inhibitors", *Angew. Chem. Int. Ed. Eng.*, 1991, 30, 613–629.

Hill, J.J. et al., "[19] Fluorescence Approaches to Study of Protein–Nucleic Acid Complexation", *Methods Enzymol.*, 1997, 278, 390–416.

Kabanov, A. V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kleparnik et al., "Fast detection of a $(CA)_{18}$ microsatellite repeat in the IgE receptor gene by capillary electrophoresis with laser–induced fluorescence detection", *Electrophoresis*, 1998, 19, 249–255.

Kroschwitz, J.I., "Polynucleotides", *Concise Encyclopedia of Polymer Science and Engineering*, 1990, John Wiley & Sons, New York, 858–859.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Luckey et al., "High speed DNA sequencing by capillary electrophoresis", *Nucl. Acids Res.*, 1990, 18(15), 4417–4421.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan, M. et al., "Lipidic Nucleic Acids", *Tetrahedron Letts.*, 1995, 36, 3651–3654.

Manoharan M. et al., "Cholic Acid–Oligonucliotide Conjugates for Antisense Applications", *Bioorganic Med. Chem. Letts.*, 1994, 4, 1053–1060.

Manoharan, M. et al., "Chemical Modifications to Improve Uptake and Bioavailability of Antisense Oligonucleotides", *Annals NY Acad. Sciences*, 1992, 660, 306–309.

Manoharan M. et al., "Oligonucleotide Conjugates: Alteration of the Pharmacokinetic Properties of Antisense Agents", *Nucleosides and Nucleotides*, 1995, 14, 969–973.

Martin, P., "Ein neuer Zugang zu 2'–O–Alkylribonucleosiden und Eigenschaften deren Oligonucleotide", *Helvetica Chemica Acta*, 1995, 78, 486–504.

Mishra, R.K. et al., "Improved leishmanicidal effect of phosphorotioate antisense oligonucleotides by LDL–medicated delivery", *Biochim. Et Biophysica*, 1995, 1264, 229–237.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Rose et al., "Characterization of Antisense Binding Properties of Peptide Nucleic Acids by Capillary Gel Electrophoresis", *Anal. Biochem.*, 1993, 65, 3545–3549.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Shea, R.G. et al., "Synthesis, hybridization properties and antiviral activity of lipid–oligodeoxynucletide conjugates", *Nucl. Acids Res.*, 1990, 18, 3777–3783.

Sigman et al., "Targeted Chemical Nucleases", *Acc. Chem. Res.*, 1993, 26, 98–104.

Svinarchuk, F.P. et al., "Inhibition of HIV proliferation in MT–4 cells by antisense oligonucleotide conjugated to lipophilic groups", *Biochimie*, 1993, 79, 49–54.

Thormann, W., "Capillary Electrophoretic Separations", *Protein Purification: Principles, High–Resolution Methods, and Applications*, Second Edition, Janson et al. (eds.), VCH Publishers, New York, New York, 1998, Ch. 17, 603–650.

Wickstrom, E., "Oligodeoxynucleotide stability in subcellular extracts and culture media", *J. Biochem. Biophys. Methods*, 1986, 13, 97–102.

Wu et al., "Analysis of Cyanine Dye–Labeled PCR Product and Restriction Fragments by Capillary Electrophoresis and Laser–Induced Fluorescence", *Clin. Chem.*, 1997, 43(9), 1660–1662.

Crooke et al. (eds.), *Antisense Research and Applications*, CRC Press, Boca Raton, 1993.

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
tttttttttt tttttttt                                                      19

FLUORESCENCE BASED NUCLEASE ASSAY

FIELD OF THE INVENTION

The present invention relates to the field of diagnostic and analytic methods for detection and quantification (quantitation) of nucleic acid species having specific nucleobase sequences, and to the use of capillary gel electrophoresis for such detection. More specifically, the present invention is directed to the use of capillary gel electrophoresis coupled with laser-induced fluorescence detection for the quantitative determination of nuclease stability of oligomeric compounds including oligonucleotides, oligonucleotide analogs, and chain shortened deletion sequences resulting from nuclease degradation of parent species. In further embodiments, the present invention relates to methods for determining the relative binding affinity of one or more oligomeric compounds for a substrate having nuclease activity, and to methods for determining the nuclease activity of an enzyme

BACKGROUND OF THE INVENTION

Oligonucleotides and oligonucleotide analogs (hereinafter referred to as "oligomeric compounds") of known sequences are utilized in a wide variety of chemical and biological applications, including PCR (polymerase chain reaction) and molecular cloning, as well as in the diagnosis and treatment of diseases (see, for example, *Antisense Research and Applications*, Crooke and Lebleu, eds., CRC Press, Boca Raton, 1993). It is often desirable to detect, isolate and/or quantitate a specific, desired oligomeric compound present in a complex mixture which may also include other closely related oligomeric compounds. Such other closely related oligomeric compounds may be less than full length as compared to the oligomeric compound of interest but otherwise have the same sequence, or may differ from a desired sequence by one or only a few bases. This is especially important in biological samples, where the presence or absence of specific known nucleotide sequences can be indicative of the presence or absence of an added oligonucleotide agent or, alternatively, a disease state. It is also important in assays to determine the effect of particular enzymes on selected oligomeric compounds, especially in cases where enzymes possess nuclease activity. The foregoing considerations are also important in the manufacture of oligonucleotides, for example, to characterize the purity of the product.

Techniques for the detection and quantification of oligomeric compounds are known. However, samples of interest often do not contain sufficient concentrations of oligonucleotides to permit detection by techniques such as ultraviolet (UV) spectroscopy. Additionally, samples often contain other absorbing species that prohibit detection of the species of interest. Other analytic techniques may lack specificity for a particular nucleic acid sequence, or require excessive sample preparation or analysis times.

The use of electrophoretic techniques to separate oligonucleotide species is documented in the literature. One such technique is capillary electrophoresis (CE), which employs relatively long, thin capillary columns for the separation of oligonucleotides. See generally, *Capillary Electrophoresis Theory and Practice*, P. Grossman and L. Colburn, eds. Academic Press, New York (1992), and Janson Ryden, *Protein Purification*, Ch. 17, VCH Publishers, New York, N.Y. CE affords several advantages over conventional electrophoretic techniques such as polyacrylamide gel electrophoresis (PAGE). for example, because CE is performed in very small diameter tubing (typically 50–100 $\mu$m i.d.), electric fields 10 to 100 fold greater than those used in conventional electrophoretic systems can be applied because of reduced Joule heating. This affords very high run speeds and improved resolution. Also, CE lends itself to on-column detection means including ultraviolet (UV) spectroscopy, amperometric measurement, conductivity measurement, laser-induced fluorescence detection (LIF) or thermooptical detection. Additionally, CE can be performed with or without a gel medium in the capillary. The use of electrophoretic techniques to separate oligonucleotide species using gels such as polyacrylamide gel is referred to as capillary gel electrophoresis (CGE).

There have been several reports of the use of CE in the detection of DNA species, such as in the high speed sequencing of DNA. For example, Luckey et al., Nucleic Acids Research, 1990, 18, 4417–4421, describes a CE instrument developed for automated DNA sequencing in which products are detected via the fluorescence of an intercalating dye.

CE analysis of PCR amplified DNA has been reported using non-gel sieving buffers and fluorescent intercalating dyes. The identification of DNA molecules by pre-column hybridization followed by capillary electrophoresis with on-line fluorescence detection has been described (Chen et al., *Journal of Chromatography*, 1991, 559, 295–305).

CGE has been used to separate peptide nucleic acid (PNA)-oligonucleotide heteroduplexes from free single-strand oligonucleotide and single strand peptide nucleic acid (Rose et al., Anal. Biochem., 1993, 65, 3545–3549). PNAs are capable of hybridization to complementary DNA or RNA sequences to form hybridized moieties which are more stable (i.e., which have higher binding affinities and higher melting temperatures) than corresponding "natural" duplexes. See *Antisense Research and Applications*, Crooke and Lebleu, eds., CRC Press, Boca Raton, 1993.

Central to the development of antisense therapeutics possessing useful pharmacological activity is the issue of nuclease resistance. Nucleases are enzymes which degrade nuclei acids into smaller pieces. For example, endonucleases cleave nucleic acids at internal sites (the phosphodiester bonds) in the nucleotide sequence. Exonucleases, on the other hand, cleave nucleotides sequentially from the free ends of linear nucleic acids. It has been well documented in the literature that short, unmodified oligonucleotides are inherently unstable in biological systems (as first reported by Wickstrom, E. *J. Biochem. Biophys. Methods*, 1986, 13, 97). This was demonstrated by showing that the half life of a short, unmodified oligonucleotide in fetal calf serum was less than half of an hour.

Nuclease stability assays are one of several screens typically performed to evaluate the usefulness of new antisense compounds. For example, nuclease stability assays are used to determine if the stability of an oligonucleotide analog to nucleases is greater than that of unmodified oligonucleotide. Nuclease stability assays are one of several screens done in an attempt to evaluate the usefulness of new antisense chemistries.

Because of the possibility that endogenous nuclease activity can degrade an oligonucleotide therapeutic before it can exert its beneficial effects, oligomeric compounds which are highly susceptible to nuclease activity are, in most situations, less desirable than those which are nuclease resistant. However, it is often difficult to determine the nuclease stability of an oligomeric compound in a solution containing many components using present methods.

Therefore, there exists a long-felt need for methods of detecting and quantifying products of nuclease digestions of target oligomeric compounds to ascertain determine the nuclease stability of the compounds (i.e., "determining the nuclease stability") the nuclease stability of oligomeric compounds that overcome the limitations posed by present methods. The present invention is directed to these, as well as other, important ends.

SUMMARY OF THE INVENTION

The present invention advantageously provides analytical techniques for, inter alia, determining nuclease stability of oligomeric compounds. In preferred embodiments of methods of the invention, the resolving power and superior resolution of CGE are applied in a quantitative fashion in the analysis of oligomeric compounds and their deletion sequences present in complex mixtures.

In some preferred embodiments, methods are provided for determining the nuclease stability of an oligomeric compound comprising:

(a) digesting said oligomeric compound with a nuclease;

(b) performing capillary electrophoresis on the product of said digestion; and (c) detecting and quantifying at least one component of said digestion;

thereby determining said nuclease stability of said oligomeric compound;

wherein said components are detected using laser-induced fluorescence.

In some preferred embodiments, said oligomeric compound comprises a fluorescent label. In further preferred embodiments, the oligomeric compound is an oligonucleotide. In further preferred embodiments, steps (a), (b) and (c) are performed a plurality of times using differing concentrations of said oligomeric compound.

In other preferred embodiments, methods are provided for determining the nuclease stability of an oligomeric compound comprising the steps of:

(a) preparing an aqueous buffer solution including one or more fluorescently labeled oligomeric compounds;

(b) adding to said solution one or more nucleases to form an assay mixture;

(c) removing aliquots of said assay mixture at selected time points;

(d) inactivating said nuclease in said aliquots;

(e) performing capillary electrophoresis on said aliquots to separate components thereof; and (f) detecting and quantifying at least one of said components using laser-induced fluorescence;

thereby determining said nuclease stability of said oligomeric compound.

In some preferred embodiments, the methods of the invention further comprise performing steps (a) through (f) a plurality of times using differing concentrations of said fluorescently labeled oligomeric compounds.

In further preferred embodiments of the methods of the invention, said aqueous buffer solution includes one fluorescently labeled oligomeric compound.

In some preferred embodiments of the foregoing methods, said assay mixture comprises from about 5% to about 20% of aqueous 500 mM Tris-HCl, pH 7.5, and 80 mM $MgCl_2$ buffer (hereinafter "10× buffer"), from about 5 nM to about 40 $\mu$M fluorescently labeled oligomeric compound, and from about $1 \times 10^{-7}$ to about $1 \times 10^{-3}$ units per mL of a nuclease.

In more preferred embodiments, said assay mixture comprises from about 10% to about 15% 10× buffer, from about 10 nM to about 30 $\mu$M fluorescently labeled oligomeric compound and from about $1 \times 10^{-6}$ to about $1 \times 10^{-4}$ units per mL of a nuclease.

In still further preferred embodiments, said assay mixture comprises about 10% 10× buffer, from about 10 nM to about 20 $\mu$M fluorescently labeled oligomeric compound and about $1.6 \times 10^{-5}$ units per mL of a nuclease.

In some preferred embodiments, said nuclease is a 3' or 5'-exonuclease. In other preferred embodiments, said nuclease is an endonuclease.

In some preferred embodiments, said inactivation of said nuclease is by heating, preferably by immersion into boiling water.

In some preferred embodiments, the volume of each of said aliquots is about 10 $\mu$L.

Some more preferred embodiments of the methods of the invention further comprise diluting said inactivated aliquots prior to capillary electrophoresis. Preferably, said dilution is about twenty-fold. In more preferred embodiments, said dilution of said aliquots is from an original volume of about 10 $\mu$L to a final volume of about 200 $\mu$L.

Also provided in accordance with the present invention are methods for determining the relative binding affinity of one or more oligomeric compounds for a substrate having nuclease activity comprising the steps of:

(a) preparing a first aqueous solution including a fluorescently labeled oligomeric compound and a buffer;

(b) preparing a second aqueous solution including said fluorescently labeled oligomeric compound, one or more inhibitors, and a buffer;

(c) independently treating said first and said second aqueous solutions with one or more substrates with nuclease activity to form a first assay mixture and a second assay mixture;

(d) removing aliquots at selected time points from said first and second assay mixtures;

(e) inactivating said nuclease in said aliquots;

(f) performing capillary electrophoresis on each of said aliquots to separate components thereof;

(g) detecting and quantifying at least one of said components using laser-induced fluorescence; and (h) comparing the results of said first and said second assay mixtures to determine the relative binding affinity of said fluorescently labeled oligomeric compound.

Some preferred embodiments of the methods further comprise performing steps (a) through (h) a plurality of times using differing concentrations of inhibitor in said second aqueous solution.

In some preferred embodiments, said assay mixture comprises from 5% to about 20% 10× buffer, from about 5 nM to about 40 $\mu$M fluorescently labeled oligomeric compound, from about 5 nM to about 40 $\mu$M unlabeled inhibitor and from about $1 \times 10^{-7}$ to about $1 \times 10^{-3}$ units per mL of substrate having nuclease activity.

In more preferred embodiments, said assay mixture comprises from about 10% to about 15% 10× buffer, from about 10 nM to about 30 $\mu$M fluorescently labeled oligomeric compound, from about 25 nM to about 30 $\mu$M unlabeled inhibitor and from about $1 \times 10^{-6}$ to about $1 \times 10^{-4}$ units per mL of substrate having nuclease activity.

In even more preferred embodiments, said assay mixture comprises about 10% 10× buffer, from about 10 nM to about 20 $\mu$M fluorescently labeled oligomeric compound, from about 50 nM to about 20 $\mu$M unlabeled inhibitor and about $1.6 \times 10^{-5}$ units per mL of substrate having nuclease activity.

In some preferred embodiments, said substrate is a 3' or 5'-exonuclease. In other preferred embodiments, said substrate is an endonuclease.

In some preferred embodiments, said inactivation of said nuclease is by heating, preferably by immersion into boiling water.

In some preferred embodiments, the volume of each of said aliquots is about 10 µL.

Some preferred embodiments of the methods of the invention further comprising diluting the aliquots prior to electrophoresis. Preferably said diluting is about 20-fold.

In some preferred embodiments, said diluting is from an original volume of about 10 µL to a final volume of about 200 µL.

The present invention also provides methods for determining the nuclease activity of an enzyme comprising the steps of:

(a) preparing an aqueous buffer solution including one or more fluorescently labeled oligomeric compounds;

(b) adding to said solution an enzyme suspected of having nuclease activity to form an assay mixture;

(c) removing aliquots at selected time points from said assay mixture;

(d) inactivating said nuclease activity in said aliquots;

(e) performing capillary electrophoresis on said aliquots to separate components thereof; and (f) detecting and quantifying said components using laser-induced fluorescence;

thereby determining said nuclease activity.

Some preferred embodiments of the methods of the invention further comprise performing steps (a) through (f) using differing concentrations of fluorescently labeled oligomeric compounds.

In some preferred embodiments, said assay mixture comprises from about 5% to about 20% 10x buffer, from about 5 nM to about 40 µM fluorescently labeled oligomeric compound and an enzyme suspected of having nuclease activity.

In further preferred embodiments, said assay mixture comprises from about 10% to about 15% 10x buffer, from about 10 nM to about 30 µM fluorescently labeled oligomeric compound and an enzyme suspected of having nuclease activity.

In still further preferred embodiments, said assay mixture comprises about 10% 10x buffer, from about 10 nM to about 20 µM fluorescently labeled oligomeric compound and an enzyme suspected of having nuclease activity.

In some preferred embodiments, said inactivation of nuclease is by heating, preferably by immersion into boiling water.

In some preferred embodiments, the volume of each of said aliquots is about 10 µL.

Some further embodiments of the methods of the invention further comprise diluting said aliquots prior to electrophoresis. Preferably said diluting is about 20-fold.

In more preferred embodiments of the methods of the invention, said diluting is from an original volume of about 10 µL to a final volume of about 200 µL.

DESCRIPTION OF PREFERRED EMBODIMENTS

In some preferred embodiments, the present invention provides novel methods for the determination of nuclease stability of an oligomeric compound. The methods further provide for the quantitative determination of the relative abundance of species derived from nuclease degradation of the oligomeric compound or compounds under investigation.

In further preferred embodiments, the methods provide for direct sampling of an assay mixture at various time points, and detection of species including fluorescently labeled full length and fluorescently labeled less-than-full length oligomeric compounds. In particular, the methods are useful for determination of the nuclease stability of oligomeric compounds in solutions containing one or more enzymes.

In some preferred embodiments, the methods of the invention include:

(a) digesting said oligonucleotide with a nuclease;

(b) performing capillary electrophoresis on the product of said digestion; and (c) detecting and quantifying at least one component of said digestion, thereby determining said nuclease stability of said oligonucleotide;

wherein said components are detected using laser-induced fluorescence.

As used herein, the term "digesting said oligonucleotide with a nuclease" means contacting a nuclease with an oligonucleotide of interest, which preferably has a fluorescent label, with under conditions which facilitate the enzymatic activity of the nuclease, to form an assay mixture. Procedures for such nuclease digestions, including selection of digestion buffer systems, cofactors and the like, are well documented in the literature, and will be apparent to those of skill in the art. The nuclease and oligonucleotide and nuclease can be contacted by any convenient means for example, in some preferred embodiments, a nuclease is added to a previously prepared aqueous solution containing one or more oligonucleotides of interest and one or more buffers. The nuclease can be added in any convenient form, such as, for example, in solution, alone or with buffer, or as a solid.

The assay mixture containing the nuclease and oligonucleotide is maintained under conditions of temperature appropriate for enzymatic activity to occur. In some preferred embodiments, aliquots of the assay mixture are withdrawn from the assay mixture at selected time intervals, and the nuclease therein is inactivated by any of a number of techniques known in the art. There include, for example, by heating or by adding one or more agents that inactivate or otherwise interfere with the activity of the nuclease.

Capillary electrophoresis is then performed on the inactivated aliquots to separate components thereof (i.e., to separate products of the digestion), and the labeled components of the aliquots are detected and quantified using laser induced fluorescence. Those of skill in the art will appreciate that the amount of cleavage products formed, or the disappearance of full length oligomeric compound, over time, is a measurement of the nuclease stability of the full length oligomer. The nuclease stability of the oligomeric compound is then expressed from these data, or, in some more preferred embodiments, from such data obtained from a plurality of assay runs performed with differing concentrations of oligomeric compound.

Thus, in some preferred embodiments, the methods of the invention comprise the steps of:

(a) preparing an aqueous buffer solution including one or more fluorescently labeled oligomeric compounds;

(b) adding to said solution one or more nucleases to form an assay mixture;

(c) removing aliquots of said assay mixture at selected time points;

(d) inactivating said nuclease in said aliquots;

(e) performing capillary electrophoresis on said aliquots to separate components thereof; and (f) detecting and quantifying at least one component using laser-induced fluorescence;

thereby determining said nuclease stability.

As used herein, the term "nuclease stability" means the susceptability to degradation of a target oligomeric compound by nuclease activity. In some preferred embodiments, nuclease stability is expressed in term of the rate of appearance of one or more cleavage products, or the disappearance of full-length oligomeric compound, over time. In some preferred embodiments, the nuclease stability can be expressed in terms of concentration-based rates. For example, the CG LIF data can first analyzed to ascertain the concentration of cleavage products that occur. For example, the electropherogram can be initially integrated using, for example, Caesar software (V.6), CE Solutions, New Jersey, to determine the fractional composition of each length of oligonucleotide. The fractional amount of each length can then be multiplied by the total concentration to determine the concentration of each length of oligonucleotide. The concentration of each length of oligonucleotide can then be multiplied by the number of cleavages required to produce that length oligonucleotide from the parent compound. The total number of cleavages is summed, and that forms the rate, which, because it is based on concentration, is expressed in terms of concentration rather than an absolute number.

In the methods described herein, the inactivated aliquots are typically diluted with a diluent before performing capillary electrophoresis. The diluent can be any liquid suitable for diluting the inactivated aliquots consistent with providing a sample suitable for capillary electrophoresis. Suitable diluents include, but are not limited to, water and buffer solutions. In some preferred embodiments, the aliquots have a volume of about 10 $\mu$L. Preferably, the aliquots are diluted 20-fold prior to capillary electrophoresis, to a final volume of about 200 $\mu$L.

In some preferred embodiments, the assay buffer solution includes Tris-HCl buffer, preferably at pH 7.5, and $MgCl_2$. In some preferred embodiments, the assay solution can be conveniently prepared by combining a buffer solution, and a solution containing the labeled oligonucleotide of interest, and adding thereto a solution of the nuclease. Preferably, a diluent which is preferably deionized water, is added to as required to bring the assay mixture to a desired volume.

In some preferred embodiments, the buffer solution is conveniently prepared from a concentrated buffer solution having a concentration selected to afford the desired final buffer concentration in the assay mixture. In one preferred embodiment, the concentrated buffer solution (designated herein as "10x buffer") contains 500 mM Tris-HCl, pH 7.5, and 80 mM $MgCl_2$.

In some preferred embodiments, the assay mixture contains from about 5% to about 20% of 10x buffer by volume, from about 5 nM to about 40 $\mu$M fluorescently labeled oligomeric compound, and from about $1\times10^{-7}$ to about $1\times10^{-3}$ units per mL of an agent having nuclease activity. In some more preferred embodiments, the assay mixture contains from about 10% to about 15% of 10x buffer by volume, from about 10 nM to about 30 $\mu$M fluorescently labeled oligomeric compound, and from about $1\times10^{-6}$ to about $1\times10^{-4}$ units per mL of an agent having nuclease activity. In still more preferred embodiments, the assay mixture contains about 10% of 10x buffer by volume, from about 10 nM to about 20 $\mu$M fluorescently labeled oligomeric compound and about $1.6\times10^{-5}$ units per mL of an agent having nuclease activity.

It will be appreciated by those of skill in the art that the assay mixtures described herein can be prepared in a variety of ways, using a variety of reagents. For example, the concentrations of stock solutions that can be employed to create the assay mixture, as well as the order of addition of the components of the assay mixture are not critical. It is only necessary that the components of the final assay mixtures be present in amounts appropriate to facilitate the desired nuclease activity. It is preferable that the time of commencement of nuclease activity can be reliably determined.

In some preferred embodiments of the methods of the invention, the agent having nuclease activity is a 3' or 5'-exonuclease. In other preferred embodiments of the methods of the invention, the agent having nuclease activity is an endonuclease.

Nucleases present in the aliquots of assay mixture can be inactivated in a number of ways, including, but not limited to, heating the sample, and adding a nuclease inhibitor or denaturing agent. In some especially preferred embodiments, the aliquots are heated by immersion in boiling water or by placement on a heat block.

In some preferred embodiments of the invention, competition experiments with non-labeled oligonucleotides (e.g., non-fluoresceinated oligonucleotides in cases where the label employed is fluorescein) are performed to determine relative binding affinities. In such embodiments, selected oligomeric compounds are co-incubated in an assay mixture with modified molecules with no fluorescent tag and the relative binding affinities of the two molecules is calculated. Accordingly, the present invention also provides methods for determining the relative binding affinity of one or more oligomeric compounds for a substrate having nuclease activity comprising the steps of:

(a) preparing a first aqueous solution including a fluorescently labeled oligomeric compound and a buffer;

(b) preparing a second aqueous solution including said fluorescently labeled oligomeric compound, one or more inhibitors, and a buffer;

(c) independently treating said first and said second aqueous solutions with one or more substrates with nuclease activity to form a first assay mixture and a second assay mixture;

(d) removing aliquots at selected time points from said first and second assay mixtures;

(e) inactivating said nuclease in said aliquots;

(f) performing capillary electrophoresis on each of said aliquots to separate components thereof;

(g) detecting and quantifying at least one component of said aliquots using laser-induced fluorescence; and (h) comparing the results of said first and said second assay mixtures to determine the relative binding affinity of said fluorescently labeled oligomeric compound.

Some preferred embodiments of the present invention further comprise performing steps (b) through (h) a plurality of times for using differing concentrations of inhibitor in said second assay mixture. Preferably, the inhibitor is an oligomeric or other compound having affinity for the substrate having nuclease activity. Examples of inhibitors include known nuclease inhibitors, as well as the oligomeric compound or compounds, without the fluorescent label.

In some preferred embodiments, the assay mixture contains from about 5% to about 20% of 10x buffer, from about 5 nM to about 40 $\mu$M fluorescently labeled oligomeric compound, from about 5 nM to about 40 $\mu$M unlabeled inhibitor and from about $1\times10^{-7}$ to about $1\times10^{-3}$ units per mL of an agent having nuclease activity. Preferably, the assay mixture contains from about 10% to about 15% 10× buffer, from about 10 nM to about 30 µM fluorescently labeled oligomeric compound, from about 25 nM to about 30 µM unlabeled inhibitor and from about $1 \times 10^{-6}$ to about $1 \times 10^{-4}$ units per mL of an agent having nuclease activity. More preferably, the assay mixture comprises about 10% 10× buffer, from about 10 nM to about 20 µM fluorescently labeled oligomeric compound, from about 50 nM to about 20 µM unlabeled inhibitor and about $1.6 \times 10^{-5}$ units per mL of an agent having nuclease activity.

The present invention also provides methods for determining the nuclease activity of an enzyme comprising the steps of:

(a) preparing an aqueous buffer solution including one or more fluorescently labeled oligomeric compounds;

(b) adding to said solution an enzyme suspected of having nuclease activity to form an assay mixture;

(c) removing aliquots at selected time points from said assay mixture;

(d) inactivating said nuclease activity in said aliquots;

(e) performing capillary electrophoresis on said aliquots to separate components thereof; and (f) detecting and quantifying at least one of said components using laser-induced fluorescence;

thereby determining said nuclease activity.

Some preferred embodiments of the invention further include performing steps (a) through (f) a plurality of times using different fluorescently labeled oligomeric compounds. In other preferred embodiments, a single fluorescently labeled oligomeric compound is used.

In further preferred embodiments of the invention, steps (a) through (f) are performed a plurality of times using different concentrations of the fluorescently labeled oligomeric compound or compounds.

In some preferred embodiments the assay mixture comprises from about 5% to about 20% 10× buffer, from about 5 nM to about 40 µM fluorescently labeled oligomeric compound. As used herein, the term "10× buffer" refers to a solution consisting 500 mM Tris-HCl, pH 7.5, and 80 mM MgCl2. In a preferred embodiment the assay mixture comprises from about 10% to about 15% 10× buffer, from about 10 nM to about 30 µM fluorescently labeled oligomeric compound. In a more preferred embodiment the assay mixture comprises about 10% 10× buffer, from about 10 nM to about 20 µM fluorescently labeled oligomeric compound.

Many different types of agents having nuclease activity are amenable to the methods of the present invention. These agents include a wide variety of enzymes that are known to the art skilled and, in many cases, are commercially available. Such agents include snake venom phosphodiesterase and the bovine intestinal mucosal phosphodiesterase. Agents having nuclease activity also include chemical nucleases, a number of which have been characterized and studied (see the general review article: Sigman et al., *Acc. Chem. Res.* 1993, 26, 98–104, incorporated by reference herein in its entirety).

The concentration of agents with nuclease activity is expressed in units, where 1 unit is the amount of agent with nuclease activity that will hydrolyze 1.0 µmol of bis(p-nitrophenyl)phosphate per min at pH 8.8 at 37° C.

In preferred embodiments of the methods of the invention, fluorescently labeled full length oligomeric compounds, as well as the deletion species that are produced as the result of nuclease degradation, are detected using laser-induced fluorescence ("LIF"). LIF detection is well known in the art (see for example: Kleparnik et al., *Electrophoresis*, 1998, 19, 249–255; Chmelik et al., *J. Chromatogr.*, 1997, 790, 93–100; and Wu et al., *Clin. Chem.*, 1997, 43, 1660–1662). In one particularly preferred embodiment, the laser excitation is effected at 488 nm with the resultant emission at 520 nm. It will be appreciated, however, that the different fluorescent labels will be most advantageously employed with different excitation wavelengths. The selection of appropriate wavelength of excitation for a given fluorescent label will be apparent to those of skill in the art.

Preferably, oligomeric compounds are synthesized having one or more chemically bound fluorescent labels (fluorophores) to facilitate detection by LIF. Fluorescent oligomeric compounds can be synthesized via the incorporation of commercially available fluorescently labeled phosphoramidites or by using a linker to a number of sites on an oligomeric compound. A wide variety of commercially available fluorophores exist which are suitable for use in the present invention. Fluorophores amenable to the present invention include, but are not limited to fluorescein, dansyl, fluorescamine, OPA, NDA, ethidium bromide, acridine, JOE, FAM and rhodamine. Other fluorophore precursors are sold by Molecular Probes, Inc. Eugene, OR. Additional suitable fluorophores are described in PCT application WO 92/03464, which is incorporated by reference herein in its entirety.

Chemical bonding of fluorescent labels, with or without a linking or tethering group, to oligomeric compounds, is well known in the art (see for example: Hill, J. J. and Royer, C. A., *Methods Enzymol.*, 1997, 278, 390–416; and Amann et al., *Microbiol.* Rev., 1997, 20, 191–200). Typically, the fluorescent label is attached via a covalent bond using a tethering moiety.

Linking or tethering moieties useful for attaching groups including fluorescent labels to oligomeric compounds of the invention include N-(2-bromoethyl)phthalimide, -(3-bromopropyl) phthalimide and N-(4-bromobutyl) phthalimide (Aldrich Chemical Co., Inc., Milwaukee, Wis.). Other phthalimide-protected amine compounds can be conveniently synthesized from appropriate alkyl, aralkyl or aryl halides and phthalimide. Further representative compounds include N-(7-bromoheptyl)phthalimide; -(8-bromooctyl) phthalimide; -(9-bromononyl)phthalimide; N-(10-bromododecyl)phthalimide; N-(7-bromoundecyl) phthalimide; -( 12-bromodocecyl)phthalimide; -(13-bromotridecyl)phthalimide; N-(14-bromotetradecyl) phthalimide; N-(15-bromopentadecyl)phthalimide; N-(16-bromo-hexadecyl)-phthalimide; N-(17-bromoheptadecyl) phthalimide; N-(18-bromooctadecyl)phthalimide; N-(19-bromononadecyl)phthalimide; N-(3-bromo-2-methylpropyl)phthalimide; N-(4-bromo-2-methyl-3-ethylbutyl)phthalimide; N-(3-bromo-2,2-diethyl-propyl) phthalimide; N-(4-bromo-3-propylbutyl)phthalimide; N-(10-bromo-2,8-dibutyldecyl)phthalimide; N-(8-bromo-6, 6-dimethyloctyl)phthalimide; N-(8-bromo-6-propyl-6-butyloctyl)phthalimide; N-(4-bromo-2-methylbutyl) phthalimide; N-(5-bromo-2-methylpentyl)phthalimide; N-(5-bromo-3-methylpentyl)phthalimide; N-(6-bromo-2-ethylhexyl)phthalimide; N-(5-bromo-3-penten-2-one) phthalimide; N-(4-bromo-3-methyl-2-butanol)phthalimide; N-(8-bromo-3-amino-4-chloro-2-cyanooctyl) phthalimide; N-(7-bromo-3-methoxy-4-heptanal)phthalimide; N-(4-bromo-2-iodo-3-nitrobutyl)phthalimide; N-(12-bromo-4-isopropoxydodecyl)phthalimide; N-(10-bromo-4-azido-2-nitrodecyl)phthalimide; N-(9-bromo-5-mercaptononyl) phthalimide; N-(5-bromo-4-aminopentenyl)phthalimide;

N-(5-bromo-penten-2-yl)phthalimide; N-(3-bromoallyl) phthalimide; N-(4-bromocrotyl)phthalimide; N-(3-bromopropargyl)phthalimide; N-(1-bromonaphth-4-yl) phthalimide; N-(2-bromoanthrac-7-yl)-phthalimide; and N-(2-bromophenanthr-6-yl)phthalimide. Such halide compounds are then reacted with an appropriate 2, 6 or 8-oxygen, 2, 6 or 8-sulfur or 2, 6 or 8 amine substituted purine or purine containing nucleosides. Other sites of reactivity are available on oligonucleotide analogs having non-naturally occurring sites thereon.

As used herein, the term "oligomeric compound" refers to oligonucleotides and oligonucleotide analogs. The term "oligonucleotide" refers to an oligomer or polymer of ribonucleic acid (RNA) or deoxyribonucleic acid (DNA). The term "oligonucleotide analog" refers to oligonucleotides composed of nucleobases, sugars and covalent intersugar (backbone) linkages that include at least one portion that is non-naturally-occurring. Such modified or substituted oligonucleotides are often preferred over native forms because of desirable properties including, for example, enhanced cellular uptake, enhanced affinity for nucleic acid target and increased stability in the presence of nucleases. A discussion of antisense oligonucleotides and some desirable modifications can be found, for example, in De Mesmaeker et al., *Acc. Chem. Res.*, 1995, 28, 366, incorporated herein by reference in its entirety.

As used herein, the terms "deletion sequence" or "deletion species" refers to products of the nuclease degradation of oligomeric compounds which are less than full-length.

As is known in the art, a nucleoside is a "base-sugar combination." The base portion of the nucleoside is typically a heterocyclic base. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moieties of the sugar. In forming oligonucleotides, the phosphate groups covalently link adjacent nucleosides to one another to form a linear polymeric compound. In turn, the respective ends of this linear polymeric structure can be further joined to form, for example, a circular type structure. However, open linear structures are generally preferred.

The intersugar linkages covalently join the sugar units of the oligonucleotide backbone. In naturally occurring oligonucleotides, the intersugar linkages are 3' to 5' phosphodiester linkages. In the present invention, covalent intersugar (backbone) linkages can be naturally-occurring phosphodiester linkages, non-naturally occurring covalent intersugar (backbone) linkages or any combination of naturally and non-naturally occurring linkages. Representative non-naturally occurring covalent intersugar (backbone) linkages are described below.

Examples of preferred oligonucleotides useful in the present invention include those containing modified backbones or non-natural intersugar linkages that connect the sugar units of the oligonucleotides. As used herein, oligonucleotides having modified backbones include both those that retain a phosphorous atom in the backbone, and those that do not have a phosphorous atom in the backbone. As used herein, the terms "oligonucleotide" and "modified oligonucleotide" are intended to include nucleosides that are connected by intersugar linkages that do not contain a phosphorous atom, and intersugar linkages that do contain a phosphorous atom.

Many non-phosphodiester intersugar linkages are amenable to the present invention including phosphorothioates, chiral phosphorothioates, phosphorodithioates, phosphotriesters, aminoaklylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. The various salts, mixed salts and free acids forms of the foregoing are also preferred.

Representative United States patents that teach the preparation of the above phosphorous atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred oligomeric compounds having one or more modified internucleoside linkages that do not include a phosphorous atom therein have backbones that are formed by short chain alkyl or cycloalkyl intersugar linkages, mixed hetero atom and alkyl or cycloalkyl intersugar linkages or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of oligomeric compounds that have one or more internucleoside linkages that don't include phosphorus include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

Oligomeric compounds amenable to the present invention can include heterocyclic base (often referred to in the art as "nucleobase" or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases including but not limited to 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering, pages 858–859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligonucleotide analogs of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton,1993, pp. 276–278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned, and each of which is herein incorporated by reference, and commonly owned and allowed U.S. patent application Ser. No. 08/762,588, filed Dec. 10, 1996, also herein incorporated by reference.

Other oligomeric compounds that are amenable to the present invention include gapped or chimeric oligomeric compounds. Such compounds have been referred to in the art as "hybrids" or "gapmers." Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and each of which is herein incorporated by reference, and commonly owned and allowed U.S. patent application Ser. No. 08/465,880, filed Jun. 6, 1995, also herein incorporated by reference.

Representative sugar modifications that are amenable to the present invention include 2' modifications such as OH, F, O—, S—, or N-alkyl, O—, S—, or N-alkenyl, or O, S— or N-alkynyl, wherein the alkyl, alkenyl and alkynyl are substituted or unsubstituted $C_1$ to $C_{10}$ alkyl or $C_2$ to $C_{10}$ alkenyl and alkynyl, particularly $O[(CH_2)_nO]_mOCH_3$, $O(CH_2)_nOCH_3$, $O(CH_2)_nNH_2$ or $O(CH_2)_nCH_3$ where n and m are from 1 to about 10. Other 2' modifications include $C_1$ to $C_{10}$ lower alkyl; substituted lower alkyl, alkaryl, araalkyl, O-alkaryl or O-araalkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy, i.e., an alkoxyalkoxy group (2'-O—$CH_2CH_2OCH_3$, also known as 2'-O—( 2-methoxyethyl)) (Martin et al., Helv. Chim. Acta, 1995, 78, 486). Other preferred modifications include 2'-methoxy (2'-O—$CH_3$), 2'-aminopropoxy (2'-$OCH_2CH_2CH_2NH_2$) and 2'-fluoro (2'-F).

Additional preferred sugar substituents include those disclosed in U.S. application entitled "RNA Targeted 2'-modified Oligonucleotides That Are Conformationally Preorganized" filed Jul. 27, 1998 (Ser. No. 09/123,108); U.S. Application entitled "Aminooxy-modified Oligonucleotides" filed Jan. 30, 1998 (Ser. No. 09/016,520); U.S. application entitled "Aminooxy-modified Oligonucleotides And Methods For Making Same" filed Aug. 7, 1998 (Ser. No. 09/130,973); and U.S. application entitled "2'-o-dimethylaminoethyloxyethyl-modified Oligonucleotides" filed Aug. 7, 1998 (Ser. No. 09/130,566). Each of the foregoing applications is commonly owned by the assignee of the present application. The contents of each of the foregoing applications are hereby incorporated by reference in their entirety.

Oligomeric compounds amenable to the present invention also include those that have a chemical link to one or more moieties or conjugates which enhance the activity, cellular distribution or cellular uptake. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Let., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylamino-carbonyl-oxycholesterol moiety (Crooke et al., J. Pharmacol. Exp. Ther., 1996, 277, 923), all references incorporated herein by reference.

Representative United States patents that teach the preparation of oligomeric compounds having conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

Oligomers according to the invention preferably have from 5 to about 50 nucleobases, with 10 to 30 nucleobases being preferred and 15 to 20 nucleobases being especially preferred.

The methods of the invention can be practiced using commercially available electrophoretic apparatus, produced for example by LKB (Bromma, Sweden) and Beckman Instruments (Fullerton, Calif.). The methods of the invention also can be practiced using a wide variety of commercially available capillary electrophoresis columns.

A variety of lasers are amenable to use in the present invention. In some more preferred embodiments, the laser is a P/ACE System Laser Module 488 from Beckman Instruments.

The nuclease stability assay methods of the invention are particularly useful for the quantitative determination of the effect of a new modification, and the comparison of the effect of such modification to other chemistries.

The CGE LIF assay assay methods described herein overcomes limitations inherent in existing procedures in that no pre-treatments or purifications are required. Aliquots are analyzed directly from test solutions, allowing the direct calculation of the actual concentration of the oligomeric compound or compounds of interest. The calculation is easily made by multiplying the percent detected by the starting concentration. Although comparable results are obtained from both the present invention and traditional methods, e.g., radiolabeled slabgel electrophoresis, the present methods are superior to radiolabeled slabgel electrophoresis because the use of radioisotopes is eliminated. Further, the present methods are less labor-intensive and more amenable to automation than are radiolabeled slabgel electrophoresis.

The present methods also overcome limitations inherent in CGE analysis using ultra violet detection. Ultra violet detection is less sensitive than LIF detection and therefore requires the use of larger amounts of samples. The analysis of samples using CGE-UV also requires additional steps including a membrane desalting step (referred to as "Paulus paper"). This desalting step has been reported to alter the composition of the metabolites in the sample undergoing quantitation. Therefore, CGE analysis using UV detection supplies qualitative rather than quantitative results (see Bruin et al., J. Chromatogr. A., 1995, 709, 181–195).

Additional advantages and novel features of this invention will become apparent to those skilled in the art upon examination of the examples thereof provided below, which should not be construed as limiting the appended claims.

EXAMPLES

Example 1

General Procedure for Nuclease Assay by CGE Using Laser-induced Fluorescence (LIF) Detection The preparation of an assay mixture includes a buffer, a selected fluorescently labeled oligomeric compound, an optional inhibitor such as an unlabeled oligomeric compound or other compound, and an agent having nuclease activity such as one or more enzymes.

Assay mixtures are prepared having the following components:

fluorescently labeled oligonucleotide (~35 nM);
10× buffer (500 mM Tris-HCl, pH 7.5, and 80 mM $MgCl_2$);
deionized water;
selected inhibitors; and
selected enzyme or enzymes.

Assay mixtures are routinely prepared to a final volume of 100 μL using deionized water as the diluent. The 10× buffer is routinely used at 10% of the final volume. Other components are varied according to the desired concentration of substrates and inhibitors. If more than five time points are taken in a given assay the initial concentration is adjusted to maintain a minimum of 50 μL final volume after the final time point.

A representative assay procedure includes:

Preparing about 90 μL aqueous solution of all reagents except the nuclease agent in a 500 μL polypropylene microfuge tube;

Adding 10 μL diluted nuclease agent;

Mixing by vortexing and incubate at 37° C.;

At specified time points removing 10 μL aliquots and placing them in a boiling water bath for at least two minutes to inactivate the nuclease;

Removing the inactivated aliquots from the boiling water bath and adding 200 μL deionized water thereto; and Injecting at least some of the diluted aliquots onto a capillary electrophoresis column, and perform capillary electrophoresis.

A preferred CGE instrument is the Beckman P/ACE System MDQ Capillary Electrophoresis instrument, with a P/ACE System Laser Module 488. A preferred capillary and gel are Beckman ssDNA replaceable gel order #477621 and coated capillary #477477. The buffer used is the Tris-Borate Urea buffer from Beckman (#338481) although the urea is used at one-half the concentration recommended by Beckman in the buffer (3.5M rather than 7 M) in order to lower salt build up. The gel is made up with buffer containing 7M urea in order to attain good separation. Detection of the labeled full length and deletion sequences is by LIF with the excitation at 488 nm and the emission at 520 nm.

Analytical Methods

Data is analyzed by determining the concentration of cleavage products that occur. A compound that is shorter than the starting material by one nucleotide has had one cleavage. A compound that is shorter than the starting material by two nucleotides has had two cleavages, and so on. The electropherogram is initially integrated using Caesar software (V.6), CE Solutions, New Jersey, to determine the fractional composition of each length of oligonucleotide. The fractional amount of each length is multiplied by the total concentration to determine the concentration of each length of oligonucleotide. Then the concentration of each length of oligonucleotide is multiplied by the number of cleavages required to produce that length oligonucleotide from the parent compound. The total number of cleavages is summed and that forms the rate. Because the rate is based on concentration, rate is expressed in terms of concentration rather than an absolute number.

The rapid determination of nuclease stability of novel oligonucleotides and oligonucleotide analogs incorporating modifications to enhance their resistance to nucleases has been performed using the CGE-LIF assay method described herein. The CGE-LIF assay method has provided faster and less costly results than currently used methods that provide comparable levels of detection such as radiolabeling methods.

Example 2

Determination of $K_m$ for Bovine Intestinal Mucosal Phosphodiesterase

The $K_m$ (affinity for the substrate) and $V_{max}$ (concentration of substrate at which an enzyme exhibits half-maximal velocity) were determined for bovine intestinal mucosal phosphodiesterase using T19 diester (SEQ ID NO:1) as the substrate. For this example, the T19 diester was labeled with a fluorescein group at the 5' end of the molecule, prepared using commercially available fluoresceinated phosphoramite, available from Biogenics, San Ramon, Calif., according to standard oligonucleotide synthetic procedures.

Ten assay mixtures were prepared each having reagents at identical concentrations except for the concentration of the T19 diester. The concentration of the T19 diester varied in for each assay mixture (25 nM, 50 nM, 100 nM, 250 nM, 500 nM, 1 M, 2 M, 5 M, 10 M, and 20 M). In each assay mixture, 20 μL of 10× buffer (500 mM Tris-HCl, pH 7.5, and 80 mM MgCl$_2$) was added. Each of the 10 assay mixtures was diluted to a total volume of 180 μL with deionized water. At time zero, 20 μL of bovine intestinal mucosal phosphodiesterase enzyme was added to yield a final volume of 200 μL for each of the 10 assay mixtures. A stock solution of the enzyme was prepared as a 1:10$^5$ dilution of the product as purchased from Sigma. A 20 μL aliquot of this stock solution was used in a final volume of 200 μL (10× dilution).

At 1, 5, 10, 20, and 30 minute time points, 10 μL aliquots were removed from each assay mixture, placed in a 500 μL microfuge tube, and placed in a boiling water bath to inactivate the nuclease. After about 2 minutes the aliquots were removed from the boiling water bath and diluted with 200 μL of deionized water. Samples were stored at −20° C. until analysis by CGE-LIF.

Samples were injected onto the capillary (Beckman ssDNA replaceable gel order #477621 and coated capillary #477477). The CGE instrument was a Beckman P/ACE System MDQ Capillary Electrophoresis instrument with a P/ACE System Laser Module 488. The buffer used was the Tris-borate urea buffer from Beckman (#338481) although the Urea concentration used was one-half of that recommended by Beckman in the buffer (3.5M rather than 7 M) in order to lower salt build up. The gel was made up with buffer containing 7M urea in order to attain good separation. Deletion species were detected and quantitated using laser-induced fluorescence with excitation at 488 nm and emission at 520 nm.

The data was analyzed by determining the concentration of cleavage products. A compound that is shorter than the starting material by one nucleotide has had one cleavage. A compound that is shorter than the starting material by two nucleotides has had two cleavages, and so on. The electropherogram was initially integrated using Caesar software (V.6) to determine the fractional composition of each length of oligonucleotide. The fractional amount of each length was multiplied by the total concentration to determine the concentration of each length of oligonucleotide. Then the concentration of each length of oligonucleotide was multiplied by the number of cleavages required to produce that length oligonucleotide from the parent compound. The total number of cleavages was summed yielding the concentration of cleaved products after a certain period of time. At each time point the concentration of cleavages was determined and plotted versus time.

Slope was calculated at each concentration of the T19 diester oligonucleotide. The inverses of each rate and concentration was plotted on a Lineweaver-Burke plot (L-W). As those of skill in the art will appreciate, the slope of the L-B plot is equivalent to $K_m/V_{max}$, and the $V_{max}$ is the 1/y-intercept. Thus, from the LB plot the $K_m$ and $V_{max}$ were calculated, showing the $K_m$ to be 0.7 μM. Using the traditional slab gel method with non fluoresceinated substrate, the calculated $K_m$ was 2 μM. For $K_m$ determinations the two calculated $K_m$ values in good agreement and thus validates the use of this methodology for enzyme kinetic studies.

Example 3
Determination of Relative Binding Affinities

Relative binding affinities were determined for labeled versus non-labeled oligomeric compounds in a competitive binding assay to an enzyme substrate with nuclease activity. The $K_i$ (concentration of non-labeled oligonucleotide at which an enzyme exhibits half-maximal activity) with a fluorescently labeled substrate was also determined. The fluorescently labeled used was T19 diester (SEQ ID NO: 1) with fluorescein attached at the 5' end of the molecule. The competing non-labeled oligomeric compound was TTT TTT TTT TTT TTT TT*T* T* (SEQ ID NO: 1) where each * represents a modified T wherein the modification is 2'-O-methoxyethyl, prepared according to the procedure of Martin et al., *Helv. Chim. Acta*, 1995 vol. 78 p.486 et seq., incorporated by reference herein in its entirety. The enzyme in this example was bovine intestinal mucosal hosphodiesterase.

Seven assay mixtures were prepared having identical concentrations of labeled oligonucleotide, 10× buffer, and enzyme. The competing non-fluorescently labeled oligomeric compound varied in concentration for each of the seven assay mixtures (0.0 nM, 100 nM, 500 nM, 1 μM, 5 μM, 10 μM, and 20 μM). To each assay mixture, 10 μL of 10× buffer (500 mM Tris-HCl, pH 7.5, and 80 mM MgCl$_2$) and 12.4 μL of the fluorescein labeled T19 diester was added. Each assay mixture was diluted to a volume of 90 μL with deionized water. At time zero, 10 μL of bovine intestinal mucosal phosphodiesterase enzyme was added to give a final volume of 100 μM for each of the seven assay mixtures. A stock solution of the enzyme was prepared as a 1:10$^5$ dilution of the product as purchased from Sigma. A 10 μL aliquot of this stock solution was used in a final volume of 100 μL (10× dilution).

At 1, 5, 10, and 20 minute time points, 10 μL aliquots were removed from each assay mixture, transferred to a 500 μL microfuge tube, and then placed in a boiling water bath to inactivate the nuclease. After about 2 minutes, the aliquots were removed from the boiling water bath and diluted with 200 μL of deionized water. Samples were stored at −20° C. until analysis by CGE-LIF, which was performed as indicated for Example 2.

Data was analyzed by determining the concentration of cleavage products that occurred. The electropherogram was initially integrated using Caesar software (V.6) to determine the fractional composition of each length of oligonucleotide. The fractional amount of each length was multiplied by the total concentration to determine the concentration of each length of oligonucleotide. Then the concentration of each length of oligonucleotide was multiplied by the number of cleavages required to produce that length oligonucleotide from the parent compound. The total number of cleavages was summed, yielding rate. Because rate is based on concentration, rate becomes a concentration/time rather than an absolute rate. For each sample time point the concentration of cleavage products was determined. For each concentration of competitor a line was derived using the best fit of linear regression (Microsoft Excel, Seattle, Wash.). The slope of the line was used as the relative reaction rate at that concentration of inhibitor. A plot of the relative reaction rates versus concentration of the competitor was then produced, allowing the determination of $K_i$. In this instance, $K_i$ was determined to be 0.8 μM. The closeness of this value to the calculated $K_m$ for the T19 diester compound indicates that the two compounds bind nearly equally well to the bovine intestinal mucosal enzyme.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for determining the nuclease stability of an oligomeric compound comprising:
   (a) digesting said oligonucleotide with a nuclease;
   (b) performing capillary electrophoresis on the product of said digestion; and
   (c) detecting and quantifying at least some components of said digestion;
   thereby determining said nuclease stability of said oligomeric compound;
   wherein said components are detected using laser-induced fluorescence.

2. The method of claim 1 wherein said oligomeric compound comprises a fluorescent label.

3. The method of claim 2 wherein the oligomeric compound is an oligonucleotide.

4. The method of claim 2 further comprising performing steps (a) through (c) a plurality of times using differing concentrations of said oligomeric compound.

5. The method of claim 2 further comprising performing steps (a) through (f) a plurality of times using differing concentrations of said fluorescently labeled oligomeric compounds.

6. The method of claim 5 wherein said oligomeric compound is an oligonucleotide.

7. The method of claim 5 wherein said aqueous buffer solution includes one fluorescently labeled oligomeric compound.

8. The method of claim 1 wherein said nuclease is a 3' or 5'-exonuclease.

9. The method of claim 1 wherein said nuclease is an endonuclease.

10. A method for determining the nuclease stability of an oligomeric compound comprising the steps of:
    (a) preparing an aqueous buffer solution including one or more fluorescently labeled oligomeric compounds;
    (b) adding to said solution one or more nucleases to form an assay mixture;
    (c) removing aliquots of said assay mixture at selected time points;
    (d) inactivating said nuclease in said aliquots;
    (e) performing capillary electrophoresis on said aliquots to separate components thereof; and
    (f) detecting and quantifying at least one component of said aliquot using laser-induced fluorescence;
    thereby determining said nuclease stability of said oligomeric compound.

11. The method of claim 10, wherein said assay mixture comprises from about 5% to about 20% 10× buffer, from about 5 nM to about 40 $\mu$M fluorescently labeled oligomeric compound, and from about $1 \times 10^{-7}$ to about $1 \times 10^{-3}$ units per mL of a nuclease.

12. The method of claim 10 wherein said assay mixture comprises from about 10% to about 15% 10× buffer, from about 10 nM to about 30 $\mu$M fluorescently labeled oligomeric compound and from about $1 \times 10^{-6}$ to about $1 \times 10^{-4}$ units per mL of a nuclease.

13. The method of claim 10 wherein said assay mixture comprises about 10% 10× buffer, from about 10 nM to about 20 $\mu$M fluorescently labeled oligomeric compound and about $1.6 \times 10^{-5}$ units per mL of a nuclease.

14. The method of claim 10 wherein said inactivation of said nuclease is by heating.

15. The method of claim 14 wherein said heating is by immersion into boiling water.

16. The method of claim 10 wherein the volume of each of said aliquots is about 10 $\mu$L.

17. The method of claim 10 further comprising diluting said inactivated aliquots prior to capillary electrophoresis.

18. The method of claim 17 wherein said dilution of said aliquots is about twenty-fold.

19. The method of claim 18 wherein said dilution of said aliquots is from an original volume of about 10 $\mu$L to a final volume of about 200 $\mu$L.

20. The method of claim 10 wherein said nuclease is a 3' or 5'-exonuclease.

21. The method of claim 10 wherein said nuclease is an endonuclease.

22. A method for determining the relative binding affinity of one or more oligomeric compounds for a substrate having nuclease activity comprising the steps of:
    (a) preparing a first aqueous solution including a fluorescently labeled oligomeric compound and a buffer;
    (b) preparing a second aqueous solution including said fluorescently labeled oligomeric compound, one or more inhibitors, and a buffer;
    (c) independently treating said first and said second aqueous solutions with one or more substrates with nuclease activity to form a first assay mixture and a second assay mixture;
    (d) removing aliquots at selected time points from said first and second assay mixtures;
    (e) inactivating said nuclease in said aliquots;
    (f) performing capillary electrophoresis on each of said aliquots to separate components thereof;

(g) detecting and quantifying at least one component of said aliquots using laser-induced fluorescence; and (h) comparing the results of said first and said second assay mixtures to determine the relative binding affinity of said fluorescently labeled oligomeric compound.

23. The method of claim 22 further comprising performing steps (b) through (f) a plurality of times using differing concentrations of inhibitor in said second aqueous solution.

24. The method of claim 23 wherein said oligomeric compound is an oligonucleotide.

25. The method of claim 23 wherein said second assay mixture comprises from 5% to about 20% 10× buffer, from about 5 nM to about 40 μM fluorescently labeled oligomeric compound, from about 5 nM to about 40 μM unlabeled inhibitor and from about $1\times10^{-7}$ to about $1\times10^{-3}$ units per mL of substrate having nuclease activity.

26. The method of claim 25 wherein said second assay mixture comprises from about 10% to about 15% 10× buffer, from about 10 nM to about 30 μM fluorescently labeled oligomeric compound, from about 25 nM to about 30 μM unlabeled inhibitor and from about $1\times10^{-6}$ to about $1\times10^{-4}$ units per mL of substrate having nuclease activity.

27. The method of claim 26 wherein said second assay mixture comprises about 10% 10× buffer, from about 10 nM to about 20 μM fluorescently labeled oligomeric compound, from about 50 nM to about 20 μM unlabeled inhibitor and about $1.6\times10^{-5}$ units per mL of substrate having nuclease activity.

28. The method of claim 23 wherein said substrate is a 3' or 5'-exonuclease.

29. The method of claim 23 wherein said substrate is an endonuclease.

30. The method of claim 23 wherein said inactivation of said nuclease is by heating.

31. The method of claim 30 wherein said heating is by immersion into boiling water.

32. The method of claim 31 wherein the volume of each of said aliquots is about 10 μL.

33. The method of claim 23 further comprising diluting the aliquots prior to electrophoresis.

34. The method of claim 33 wherein said diluting is about 20-fold.

35. The method of claim 34 wherein said diluting is from an original volume of about 10 μL to a final volume of about 200 μL.

36. A method for determining the nuclease activity of an enzyme comprising the steps of:

(a) preparing an aqueous buffer solution including one or more fluorescently labeled oligomeric compounds;

(b) adding to said solution an enzyme suspected of having nuclease activity to form an assay mixture;

(c) removing aliquots at selected time points from said assay mixture;

(d) inactivating said nuclease activity in said aliquots;

(e) performing capillary electrophoresis on said aliquots to separate components thereof; and (f) detecting and quantifying at least one component using laser-induced fluorescence;

thereby determining said nuclease activity.

37. The method of claim 36 further comprising performing steps (a) through (f) a plurality of times using differing concentrations of fluorescently labeled oligomeric compounds.

38. The method of claim 37 wherein said assay mixture comprises from about 5% to about 20% 10× buffer, from about 5 nM to about 40 μM fluorescently labeled oligomeric compound and an enzyme suspected of having nuclease activity.

39. The method of claim 37 wherein said assay mixture comprises from about 10% to about 15% 10× buffer, from about 10 nM to about 30 μM fluorescently labeled oligomeric compound and an enzyme suspected of having nuclease activity.

40. The method of claim 37 wherein said assay mixture comprises about 10% 10× buffer, from about 10 nM to about 20 μM fluorescently labeled oligomeric compound and an enzyme suspected of having nuclease activity.

41. The method of claim 37 wherein said inactivation of nuclease is by heating.

42. The method of claim 41 wherein said heating is by immersion into boiling water.

43. The method of claim 42 wherein the volume of each of said aliquots is about 10 μL.

44. The method of claim 37 further comprising diluting said aliquots prior to electrophoresis.

45. The method of claim 44 wherein said diluting is approximately 20-fold.

46. The method of claim 45 wherein said diluting is from an original volume of about 10 μL to a final volume of about 200 μL.

* * * * *

UNITED STATES PATENT AND TRADEMARK OFFICE
CERTIFICATE OF CORRECTION

PATENT NO. : 6,127,124
DATED : October 3, 2000
INVENTOR(S) : Leeds et al.

Page 1 of 1

It is certified that error appears in the above-identified patent and that said Letters Patent is hereby corrected as shown below:

Column 1,
Line 20, please insert -- . -- after "enzyme".

Column 2,
Line 41, please delete "nuclei" and insert therefor -- nucleic --.

Column 6,
Line 30, please insert -- . -- after "means" and delete "for" and insert therefor -- For --.

Column 10,
Line 45, please delete "N-(7-bromoundecyl)" and insert therefor
-- N-(11-bromoundecyl) --.

Column 18,
Line 20, please delete "100 μM" and insert therefor -- 100 μL --.

Signed and Sealed this

Twenty-third Day of April, 2002

Attest:

Attesting Officer

JAMES E. ROGAN
Director of the United States Patent and Trademark Office